(12) United States Patent
Yang et al.

(10) Patent No.: US 6,961,610 B2
(45) Date of Patent: Nov. 1, 2005

(54) BRANCHED POLYETHYLENE OXIDE TERMINATED BIOMEDICAL POLYMERS AND THEIR USE IN BIOMEDICAL DEVICES

(75) Inventors: Zhongping Yang, Woodbury, MN (US); Michael J. Ebert, Fridley, MN (US); James M. Anderson, Cleveland, OH (US)

(73) Assignee: Medtronic, Inc., Minneapolis, MN (US)

( * ) Notice: Subject to any disclaimer, the term of this patent is extended or adjusted under 35 U.S.C. 154(b) by 529 days.

(21) Appl. No.: 10/131,440

(22) Filed: Apr. 25, 2002

(65) Prior Publication Data

US 2003/0204230 A1    Oct. 30, 2003

(51) Int. Cl.[7] .......................... A61N 1/02; A61N 1/375
(52) U.S. Cl. ............................................ 607/2; 607/36
(58) Field of Search .............................. 607/1–5, 9, 36, 607/39–58

(56) References Cited

U.S. PATENT DOCUMENTS

| | | | |
|---|---|---|---|
| 5,282,844 A | 2/1994 | Stokes et al. ................ | 607/120 |
| 5,589,563 A | 12/1996 | Ward et al. .................... | 528/44 |
| 5,830,986 A | 11/1998 | Merrill et al. ............... | 528/332 |
| 5,855,618 A | 1/1999 | Patnaik et al. ................ | 623/11 |
| 6,046,305 A | 4/2000 | Choi .......................... | 528/491 |
| 6,812,217 B2 * | 11/2004 | Hendriks ...................... | 514/44 |
| 2003/0028224 A1 * | 2/2003 | McVenes et al. ............. | 607/36 |

FOREIGN PATENT DOCUMENTS

| | | | |
|---|---|---|---|
| WO | WO 93/25247 | 12/1993 | ........... A61L 33/00 |
| WO | WO 96/14887 | * 5/1996 | ........... A61L 27/00 |
| WO | WO 97/18904 | 5/1997 | ............ B05D 7/04 |

\* cited by examiner

*Primary Examiner*—Carl Layno
(74) *Attorney, Agent, or Firm*—Girma Wolde-Michael; Michael C. Soldner

(57) ABSTRACT

A biomedical polymer has a substantially linear base polymer; and branched polyethylene oxide covalently bonded to the base polymer as surface active end groups. The branched polyethylene oxide has at least two, more particularly at least four, and still more particularly at least six branches. Suitable base polymers include epoxies, polyurethanes, polyurethane copolymers, fluoropolymers, polyolefins and silicone rubbers. Biologically active agents may be attached to the branched polyethylene oxide. Suitable biologically active agents include microbial peptide agents, detergents, non-steroidal anti-inflammatory drugs, cations, amine-containing organosilicones, diphosphonates, fatty acids, fatty acid salts, heparin and glucocorticosteroids. The biological polymer may be used as a casing for a medical unit of an implantable medical device, such as a pacemaker. In this case, the casing at least partially encloses the medical unit.

9 Claims, 2 Drawing Sheets

BRANCHED POLYETHYLENE OXIDE TERMINATED BIOMEDICAL POLYMERS AND THEIR USE IN BIOMEDICAL DEVICES

INCORPORATION BY RERERENCE

This application incorporates by reference the contents of U.S. Pat. No. 5,589,563 to Ward et al., issued Dec. 31, 1996.

BACKGROUND OF THE INVENTION

Some functional surface modifying endgroups (SMEs), such as hydrocarbons, fluorocarbons, silicones, linear PEOs and sulfonates, have been demonstrated in biomedical polymers to improve biocompatibility and biostability. These biomedical polymers may, for example, be used as a casing to enclose an implantable biomedical device (IMD). A small concentration of the surface modifying endgroups, which terminates the ends of a base polymer, modifies the surface properties of the base polymer without significantly modifying bulk properties. Low bulk concentrations of the SME can produce essentially complete monolayer coverage.

The surface modifying endgroups (SMEs) migrate to the surface of the polymer. Thus, if the polymer is used as a casing for an implantable medical device, the end groups will migrate to the surface of the IMD. This surface develops spontaneously by surface-energy-reducing migrations of the SME to the air-facing surface. Interfacial energy continues to form the surface in response to a change in environment, e.g., following implantation into a patient and tissue contact. Surface modification is thought to reduce protein adsorption and platelet adhesion, possibly minimizing tissue encapsulation. However, current SMEs cannot provide a sufficiently think cover on the base polymer surfaces because linear molecules are used for the SMEs. It is believed that polymers having low SME coverage may be ineffective in improving long-term biocompatibility and biostability in implantable biomedical devices.

SUMMARY OF THE INVENTION

Accordingly, one possible object of the invention is to provide better coverage of surface modifying end groups on the base polymers to which they are attached.

This and other objects are accomplished by providing a biomedical polymer having a substantially linear base polymer; and branched polyethylene oxide covalently bonded to the base polymer as surface active end groups. The branched polyethylene oxide has at least two, more particularly at least four, and still more particularly at least six branches. Suitable base polymers include polyurethanes, polyurethane copolymers, fluoropolymers, polyolefins and silicone rubbers.

Biologically active agents may be attached to the branched polyethylene oxide. Suitable biologically active agents include microbial peptide agents, detergents, non-steroidal anti-inflammatory drugs, cations, amine-containing organosilicones, diphosphonates, fatty acids, fatty acid salts, heparin and glucocorticosteroids.

The biological polymer may be used as a casing for a medical unit of an implantable medical device, such as a pacemaker. In this case, the casing at least partially encloses the medical unit. The medical unit may contain a shell, perhaps formed of a different material. In this case, the polymeric casing is formed on the outer surface of the shell.

BRIEF DESCRIPTION OF THE DRAWINGS

These and other objects and advantages of the present invention will become more apparent and more readily appreciated from the following description of the preferred embodiments, taken in conjunction with the accompanying drawing of which.

DETAILED DESCRIPTION OF THE PREFERRED EMBODIMENT

Figure 1:
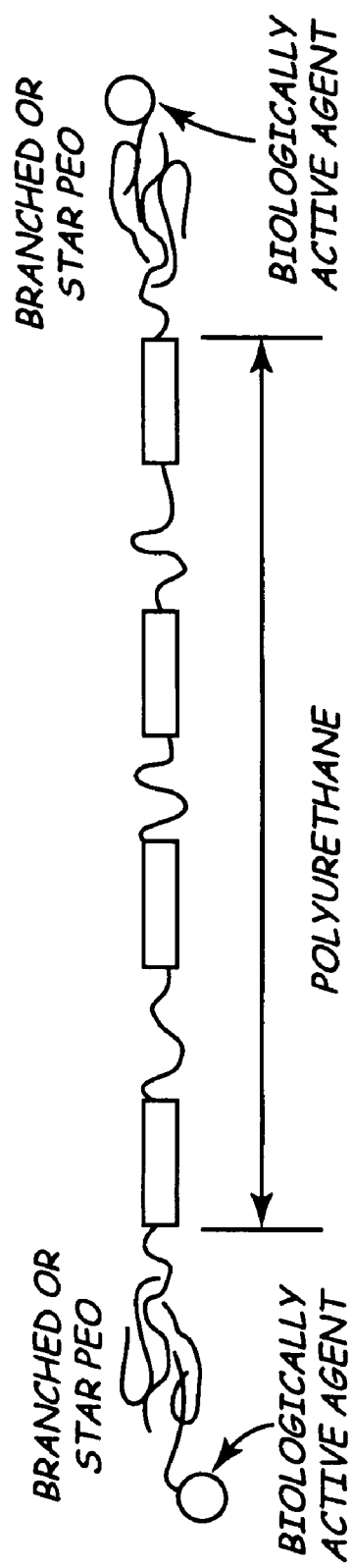
FIG. 1 is a schematic view of a base polymer having branched or star polyethylene oxide biologically modifying end units.

Reference will now be made in detail to the preferred embodiments of the present invention, examples of which are illustrated in the accompanying drawings, wherein like reference numerals refer to like elements throughout.

The inventors propose a new kind of surface modifying endgroup for biomedical polymers. Specifically, the inventors proposed using branched polyethylene oxide (PEO) or PEO star molecules to terminate biomedical polymers.

Using branched PEO molecules to terminate base polymers may significantly increase the density of the functional PEO endgroups on the surface of the implantable medical device. In turn, this may improve biocompatibilty and biostability of the IMD in bodily tissues such as blood.

FIG. 1 is a schematic view of a base polymer having branched or star polyethylene oxide biologically modifying end units. In FIG. 1, the polymer is represented by a polyurethane chain. Of course, many other suitable polymers work equally as well. At the terminal ends of the polyurethane, branched or star polyethylene oxide is provided. Whether the PEO is branched or starred depends of the number of substituents. At least two branches, more particularly, at least four branches, and still more particularly, at least six branches are provided. The term "star PEO" has been previously defined as requiring at least five branches. However, the invention should not be restricted in the definition. To some extent, the terms "branched PEO" and "star PEO" terms are used interchangeably in this discussion.

As can be seen in FIG. 1, a biologically active agent is attached to the branched or star PEO. This biologically active agent is optionally provided, representing one embodiment of the invention. The biologically active agent will be described below.

Figure 2:
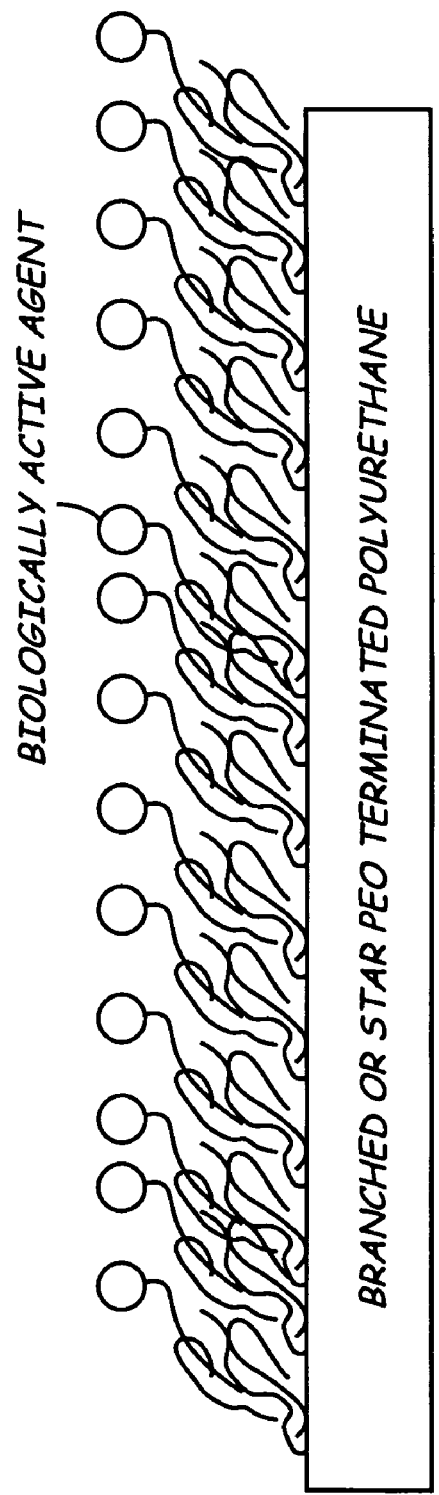
FIG. 2 is a schematic view of a biological polymer, showing an interface on the polymer, formed of branched or star polyethylene oxide, as it would appear in water or a biological fluid.

FIG. 2 is a schematic view of a biological polymer, showing an interface on the polymer, formed of branched or star PEO, as the interface would appear in water or a biological fluid. As can be seen, the PEO surface modifying end groups form a protection layer on the base polymer. As was shown in FIG. 1, FIG. 2 shows biologically active agents attached to the branched PEO groups. These biologically active agents may or may not be provided. That is, a valuable biomedical polymer casing is produced even if biologically active agents have not been added to the biomedical polymer.

The branched or star molecules can be synthesized by using dendrimers as cores, and modified polyethylene oxide as the arms extending from the cores.

Star-shaped polymers comprise several linear chains linked together at one end of each chain, constituting the simplest form of branching. The branched PEO can be formed using a plurality of different methods. For example, there exist two distinct synthetic approaches for star-shaped polymers: divergent and convergent approaches. The convergent approach, called the "arm-first method," involves the termination of growing polymer chains with multifunctional terminating agents to form the star-shaped polymer. The convergent method combined with anionic living polymerization, a newly developed technique, is known to produce a star-shaped polymer of controlled arm length, narrow molecular weight distribution, and easily varied arm number. The most common method for the synthesis of this type of polymer has involved homogeneous organolithium polymerization, followed by a linking reaction between the lithium chain end and the linking agents, such as chlorosilanes, phthalate esters, and m- and p-divinyl benzenes. The main drawback of this method is that the branches of star-shaped molecules cannot be modified with functional groups at their outer ends. Thus, if biologically active agents are to be provided, the "arm-first method" may be less desirable.

The branched or star PEO can also be made by a divergent approach. The divergent approach, also called the "core-first method," starts the synthesis reaction from a plurifunctional initiator and proceeds outward. This technique allows the modification of the branches with functional groups at their outer ends, thus providing the possibility of further reaction for forming block copolymers or selective adsorption. Due to its simplicity, the divergent method has been commonly applied for a variety of star-shaped polymers. Gellation can happen due to a cross linking reaction because proteins, in general, have several accessible amino groups.

The branched or star PEO can also be formed by a "one-arm-first method," which is described in U.S. Pat. No. 6,046,305 to Choi, which patent is hereby incorporated by a reference. The "one-arm-first method," is basically an improvement of the "arm-first method" and the "core-first method." In this method, one arm bearing a functional group is prepared first by ring-opening polymerization of ethylene oxide initiated with a heterobifunctional compound, and then the growing polymer chain end is terminated by a polyfunctional compound followed by sequential polymerization of ethylene oxide.

After the PEO branched or star molecules are formed, they can be used as surface modifying end groups for a biological polymer. The coverage of the PEO surface layer on a base polymer surface can be manipulated in a controlled way by design in the PEO star SME molecules. That is, thickness of the PEO surface layer can be controlled using known techniques to control the amount of branching and chain length in the PEO molecules.

Many different base polymers can be used with the branched or star PEO. For example, silicone rubbers, fluoropolymers, epoxies, polyamides, polyimides, polyolefins, polyurethanes and polyurethane copolymers such as polyether polyurethanes, polycarbonate polyurethanes, silicone polyurethane and the like may be used.

To attach the branched or star PEO to the base polymer as a surface modifying end group, the branched or star PEO is combined with monomer(s) that will form the base polymer. During polymerization of the monomer(s), the branched or star PEO acts as a chain terminator. U.S. Pat. No. 5,589,563 to Ward et al., issued on Dec. 31, 1996 discloses a method of attaching surface modifying end groups to base polymers for use in biological materials. The base polymer may be linear. The surface modifying end groups may be covalently bonded to the base polymer. Ward et al. uses the surface modifying end groups to achieve a surface or interfacial tension that differs by at least 1 dyne/cm from the surface or interfacial tension of an otherwise identical polymer that does not contain covalently bonded surface modifying end groups. The method of Ward et al. can be used to attach the branched or star PEO to the base polymer as a surface modifying end group.

The outer reactable ends of the branched or star PEO chains can be used for immobilizing biologically active agents, such as heparin to further enhance the biocompatibility and biostability.

Examples of other suitable biologically active agents are microbial peptide agents, detergents, non-steroidal anti-inflammatory drugs, cations, amine-containing organosilicones, diphosphonates, fatty acids fatty acid salts and glucorticosteroids.

If the surface chemistry of the biological polymers is changed or modified with a biologically active agent, such as a microbial peptide agent, an antimicrobial agent such as those synthesized with quinolone drugs (e.g. Ciprofloxacin, Norfloxacin), an antibiotic such as Gentamyacin or Zithromax, a biocompatible detergent such as Pluronic® brand PE-EO-block polymer sold by BASF, a non-steroidal anti-inflammatory drug, a cation, an amine-containing organo-silicone, a fatty acid or a fatty acid salt, bacterial adhesion to the surface of an IMD may be discouraged. For example, polyurethane and silicone rubber polymers used in bradycardia, tachycardia and neurological leads may be modified using certain adhesion reducing biologically active agent such as a detergent, salicylic acids such as aspirin or ibuprofen, other non-steroidal anti-inflammatory agents, fatty acid salts (cations) or amine-containing silicones. As modified, bacterial adhesion may be reduced acutely, chronically, and many years later when a pacemaker pulse generator is changed-out. Such agents may also have a significant benefit in preventing scar tissue adhesion to facilitate chronic removal.

Inhibition of calcification in bioprosthetic heart valves using sustained local release of calcium and sodium diphosphonates has also been reported. However, phosphonates released systemically can have adverse effects on a patient's overall growth, bone development and calcium metabolism. Immobilization of ethanehydroxydiphosphonate within a bioprosthetic heart valve as the poorly soluble Ca2+ salt inhibits calcification at drug levels insufficient to produce side effects. However, rapid time-dependent efflux of the phosphonate from the pericardial tissue limited its usefulness in long-term heart valve replacements. The use of diphosphonates as attachments to branched or star PEO SMEs may control mineralization of silicone rubber pacemaker leads, enhancing their chronic extractability.

Another use for diphosphonates is in heart valves. Specifically, polymeric heart valves have not been used because of thrombosis. A plastic heart valve could experience mineralization and infection. A leaflet heart valve made of polyurethane, with diphosphonate attached to the polyurethane, would not have the mineralization problem.

Glucocorticosteroids, such as dexamethasone or beclamethasone, are described in U.S. Pat. No. 5,282,844 issued to Stokes et al., which is hereby incorporated herein by reference in its entirety. Used as a biologically active agent attached to a branched or star PEO, glucocortico-steroids may exhibit desirable properties, for example, in relation to pacemaker leads.

The biologically active agents may be attached to the branched or star PEO SMEs either before or after the polymer is formed. That is, if the biologically active agents can withstand polymerization without degradation, they can be attached to the branched or star PEO prior to addition of the branched or star PEO to the base polymer. For example, the decomposition point of dexamethasone is about 240° C. which is above any polymerization temperature. As mentioned above, the arm first polymerization method is not suitable for manipulating the PEO with functional groups. Thus, either the core-first method or the one-arm-first method should be used in order to add biologically active agents before the branch or star PEO is attached to the base polymer.

It should be noted that it may be desirable to attach more than one different biologically active agent to the branched or star PEO. For example, a polyurethane heart valve having a diphosphonate biologically active agent and an antimicrobial biologically active agent could be made.

Biologically active agents that would otherwise degrade must be attached to the branched or star PEO after the branched or star PEO is combined with the base polymer.

As to how the biologically active agent is attached to the branched or star PEO, the method depends on the functional group of the biologically active agent. For example, steroids have three benzene rings, a five member ring and a hydroxyl group attached to the five member ring. The hydroxyl group may be a convenient place to attach the steroid to the branched or star PEO.

It should be noted that branched or star PEO has hydroxyl terminal groups. If the hydroxyl groups are not readily compatible with the functional groups on the biologically active agent, there are at least two possible solutions. First, a heterobifunctional PEO could be provided. In this manner, the PEO would have other functional groups rather than just hydroxyl groups.

A second way to deal with hydroxyl incompatibility is to add a different functional group to the hydroxyl group, which different functional group would in turn bond to the biologically active agent. For example, branched or star PEO could be immersed in a solution containing diisocyannate groups (for example, hexa-methylene diisocyannate) to react the cyannate groups with the PEO hydroxyls. Then, the diiscocyanate treated PEO could be put in another solution to react with the steroid hydroxyls. This would produce two urethane groups and a star PEO having steroid properties.

Figure 3:
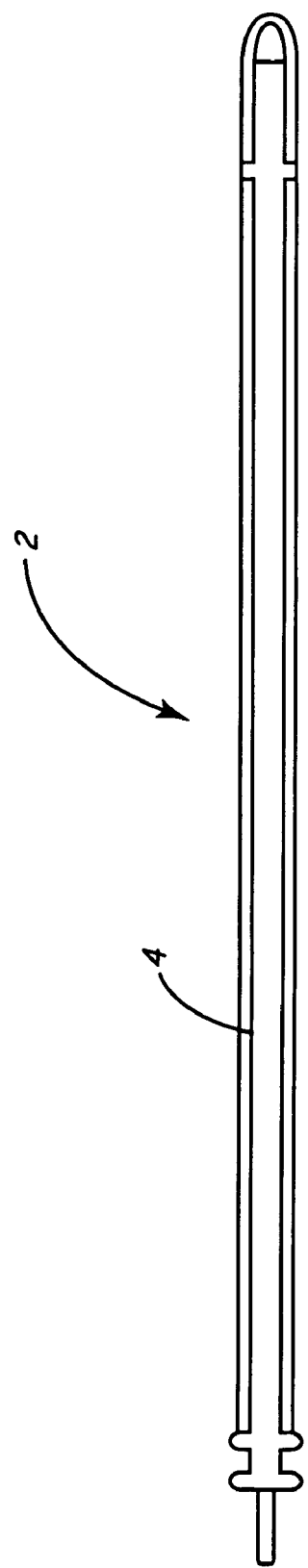
FIG. 3 is a cut away side view of a medical lead with insulation made from a polymer having surface modifying end groups.

Once the biomedical polymer, with or without biologically active agents, has been formed, the biomedical polymer can be used as a casing for an implantable medical device. This may be done through injection molding, extrusion or other known techniques. FIG. 3 is a side cutaway view of a medical lead according to one aspect of the invention. The lead, which is one example of an IMD, includes an elongated lead body 2, which is covered over at least a portion of its surface with an insulation casing 4. The insulation may be made entirely of the SME polymer, or it could have an SME polymer applied as a coating on the insulation. If the SME polymer has a very expensive component, a thin coating may be more desirable. The casing 4 is formed of a polymer having branched or star polyethylene oxide surface modifying end groups. Although a lead is shown for discussion purposes, it will be understood that the surface of other IMDs may be used, including surfaces of catheters, stents, drug delivery devices, etc.

As may be clear from the preceding paragraph, the biomedical polymer having branched or star PEO may form the outer casing of the IMD. Alternatively, the IMD may also have a shell formed of a polymeric or nonpolymeric material. In this case, the biomedical polymer casing would be formed on the shell.

It is not necessary for the coating to completely encapsulate the IMD. The coating may be formed only on surfaces that do not require a patient-IMD interface. For example, the electrodes of a pacemaker lead likely need not be encapsulated with the coating.

The invention has been described in detail with particular reference to preferred embodiments thereof and examples, but it will be understood that variations and modifications can be effected within the spirit and scope of the invention.

What is claimed is:

1. An implantable medical device, comprising:
   a medical unit; and
   a casing at least partially enclosing the medical unit, the casing being formed of a base polymer with branched polyethylene oxide attached to the base polymer as surface modifying end groups, the branched polyethylene oxide having at least two branches, wherein two different biologically active agents are attached to the branched polyethylene oxide.

2. An implantable medical device according to claim 1, wherein
   the biologically active agents are selected from the group consisting of antimicrobials, antibiotics, microbial peptide agents, biocompatible detergents, non-steroidal anti-inflammatory drugs, cations, amine-containing organosilicones, diphosphonates, fatty acids, fatty acid salts, heparin and glucocorticosteroids.

3. An implantable medical device according to claim 1, wherein the medical unit is a pacemaker lead.

4. An implantable medical device according to claim 1, wherein the base polymer is selected from the group consisting of epoxies, polyurethanes, polyurethane copolymers, fluoropolymers, polyolefins and silicone rubbers.

5. An implantable medical device according to claim 1, wherein the branched polyethylene oxide has at least four branches.

6. An implantable medical device, comprising:
   a medical unit; and
   a casing at least partially enclosing the medical unit, the casing being formed of a base polymer with branched polyethylene oxide attached to the base polymer as surface modifying end groups, the branched polyethylene oxide having at least two branches, wherein the medical unit contains a shell having an outer surface, and the casing is formed on the outer surface of the shell.

7. An implantable medical device, comprising:
   a medical unit; and
   a casing at least partially enclosing the medical unit, the casing being formed of a base polymer with branched polyethylene oxide attached to the base polymer as surface modifying end groups, the branched polyethylene oxide having at least two branches, wherein the branched polyethylene oxide has at least six branches.

8. An implantable medical device, comprising:
   a medical unit; and
   a casing at least partially enclosing the medical unit, the casing being formed of a base polymer with branched polyethylene oxide attached to the base polymer as surface modifying end groups, the branched polyethylene oxide having at least two branches, wherein the branched polyethylene oxide has cross-linked branches.

9. An implantable medical device, comprising:
a medical unit; and
a casing at least partially enclosing the medical unit, the casing being formed of a base polymer with branched polyethylene oxide attached to the base polymer as surface modifying end groups, the branched polyethylene oxide having at least two branches, wherein the branched polyethylene oxide is a heterobifunctional molecule.

* * * * *